US012733601B2

(12) United States Patent
Clevenger et al.

(10) Patent No.: US 12,733,601 B2
(45) Date of Patent: Sep. 15, 2026

(54) METHODS AND ASSAYS FOR IDENTIFYING, CREATING, AND CULTIVATING DISEASE-RESISTANT PEANUT LINES

(71) Applicants: HudsonAlpha Institute for Biotechnology, Huntsville, AL (US); Instituto Nacional de Tecnologia Agropecuaria, Buenos Aires (AR)

(72) Inventors: Josh Clevenger, Huntsville, AL (US); Walid Korani, Huntsville, AL (US); Jorge Javier Baldessari, Buenos Aires (AR)

(73) Assignees: HudsonAlpha Institute for Biotechnology, Huntsville, AL (US); Instituto Nacional de Tecnologia Agropecuaria, Alabama Buenos Aires (AR)

( * ) Notice: Subject to any disclaimer, the term of this patent is extended or adjusted under 35 U.S.C. 154(b) by 90 days.

(21) Appl. No.: 18/790,193

(22) Filed: Jul. 31, 2024

(65) Prior Publication Data

US 2025/0040501 A1 Feb. 6, 2025

Related U.S. Application Data

(60) Provisional application No. 63/530,941, filed on Aug. 4, 2023.

(51) Int. Cl.

| | |
|---|---|
| ***A01H 1/00*** | (2006.01) |
| ***A01H 5/10*** | (2018.01) |
| ***A01H 6/54*** | (2018.01) |
| ***C12Q 1/6809*** | (2018.01) |

(52) U.S. Cl.

CPC ............. *A01H 1/1255* (2021.01); *A01H 5/10* (2013.01); *A01H 6/541* (2018.05); *C12Q 1/6809* (2013.01); *C12Q 2600/13* (2013.01); *C12Q 2600/156* (2013.01)

(58) Field of Classification Search

CPC ........ A01H 1/1255; A01H 6/541; A01H 5/10; C12Q 1/6809; C12Q 2600/13; C12Q 2600/156

See application file for complete search history.

(56) References Cited

U.S. PATENT DOCUMENTS

| | | | |
|---|---|---|---|
| 8,718,950 | B2 | 5/2014 | Worthey et al. |
| 2024/0294968 | A1 | 9/2024 | Clevenger et al. |

OTHER PUBLICATIONS

Chamberlin et al. (Jun. 2022). "Identification of Germplasm Resistant to Peanut Smut." The Journal of American Peanut Research and Education Society. 67(9987-0987): 1-16. (Year: 2022).*

Blas et al. (2021). "Genetic mapping and QTL analysis for peanut smut resistance." BMC Plant Biology. 21:312. (Year: 2021).*

Ospina-Maldonado et al. (2022). "Peanut Smut: A Diagnostic Guide." Plant Health Progress 2022 23:4, 492-496 (Year: 2022).*

International Search Report and Written Opinion dated Oct. 25, 2024 of corresponding International Patent Application No. PCT/US24/40312.

De Blas, et al., U.S. Department of Agriculture: Agricultural Research Servcie, Lincoln, Nebraska, "Identification of Smut Resistance in Wild *Arachis* Species and Its Introgression into Peanut Elite Lines", May 16, 2019, pp. 1657-1665.

NCBI, "Predicted: Arachis hypogaea putative disease resistance protein At3g14460 (LOC112726310), mRNA", May 24, 2019, <URL:https://www.ncbi.nlm.nih.gov/nucleotide/XM_025775645.2?report=genbank&log$=nucltop&blast_rank=2&RID=EVFRTUJWO13>>, p. 1-3.

Massa, et al., "Genotyping tools and resources to assess peanut germplasm: smut-resistant landraces as a case study," Jan. 29, 2021, pp. 1-18.

* cited by examiner

*Primary Examiner* — Bratislav Stankovic

*Assistant Examiner* — Emily K Johnson

(74) *Attorney, Agent, or Firm* — Bradley Arant Boult Cummings LLP; Stephen H. Hall; Jessica L. Zurlo

(57) ABSTRACT

The present disclosure is directed to methods of genetically detecting or generating a peanut line that is resistant to peanut smut infection. The disclosure also relates to cultivation of smut resistant peanut lines and the cessation or prevention of peanut smut in a given geographic area.

12 Claims, 4 Drawing Sheets

Specification includes a Sequence Listing.

```
ATGGCTGGAG TTCTTGTTGG TGGAGCTTTT CTGTCTGGCT TCATTAATGT TGTCCTTGAC AGGCTCATTT CTGCTGATGC
TGTCAACTTG GTTGTGGGTA AGAAGCTTAG CTCTGACTTG GTTGAGAGGC TGAGGAATGC TCTGACAGAT GCTGGAGATC
TTGTTGATGA TGCAGAGTTC AAGCAACTGG ATAACCATGA TGTGAAGGAG TGGCTCAACT CTCTCCGTGA TGCTCTTTAC
ACTGCTGATG ACTTGCTGGA CCGCGTCTGC ACCAAAGCCG CAACTCAAAA GGTCACTCTC TTGGGTAGAA TCTTCAACTC
TGAAGATAGG CAGATGGTGA ATGAGATAGA AAGGGTGGTT AGAAGGATAG AAGATCTTGA GAACCGCAAA GGAAAGCTTG
GGCTTGAAAA GATTTCCACT GCTAGCTTCT CCTGGAAAAC TCCATCCACT TCTCTTGTAA AAGGGAATGT GTGTGGCAGG
GAGGATGACA AGAAGGCCTT AATCAAGATG CTGAATGACA ACAATGAGCA TCACCTCTCT GTCATCTCTA TTGTTGGCAT
GGGTGGTGTT GGTAAAACTA CTTTAGCTCA ATGGATGTAC AATAATGCAG AGTTGATGGA GGGATTTGAT CAGAAAGCAT
GGGTTTGTGT TTCGGAAAAC TTCAATATTG TTGAGACTAC AAGGAATATA GTAAAGCAGA TCTCTACAAA TACTCAGGAT
CTTGATAGCT TCAATTCAAT TCAAGATGCT TTGAAGAAAG GATTGTCCGA AAAGAAGTTC TTTATTGTTG TGGATGATGT
TTGGAGCAAT GATCATCATC AATGGAAGGA TTTTCTAGCC CCTTTTCAAT ATGGGGTTAA GGGAAGTACT ATTCTTCTGA
CTACTCGCAA GGTAGATGTT GGTTCAGTTG TTCAAACAAA TTATCAACCT CACTATCTCA TTCCATTATC AGAAGACTAC
TGTTGGTCAG TATTTGCAGC CAATGCTTCT TTTCCAGAAT CAAATGGGAA CCCGACACTA GAAGGAATAG GCAGAAGCAT
TGCTAGGAAG TGTGATGGTT TGCCATTAGC AGCCGAAACC CTTGGTTGCT TGTGCAGAAG GCATGATGCT AAGGAATGGG
AAAAAATCTT AAGGAGTGAT ATTTGGGGAT TTTCTACAAA TGACAGTAAG ATTGTTCCAG CATTGTTAAT TAGTTACTTT
CACCTTGCTG CACATTTGAA GCGTTGTTTT GTTCATTGTG CACTGTTTCC AAAAGATTAT CACTTTAAGA AAGATGAACT
AATTTTGTTG TGGATGGCCG AAGATCTTTT AAGACTACCA AAGAGAGGAG AGAGCTTGGA AGAGGTTGGT TGCAAGTGTT
TTGAAGAATT AGTTTCAAGG TTATTCTTTA AAAAGCTTCA AGACGATGAT GAGTATTTTG TGATGCATGA TCTCTTGCAT
GACTTGGCAA TATTCCTTGC TGGAGATTTC TATTGTAGAA TAGAAGAACT TGGTGAACAA GAGGAAAAGA TGGTTCTCAC
TCGCCATTTG TCATATTTGC CACCTGGAAG GTTAGATCAT CCAATCTCAA AAGTCTTTAA CTCCAACGCG AGGCTGGAAT
CTTTCAGGAC ATCGTTGTAT ATCGATGATT TATTCAGCAT GGAAAGTGTA GCATCTAAGT TTATATGCAT GAGAGTTTTA
TCCTTTCATA AACTTGATGT ATTACCTGAT TCAATAGGTG AATCGATTCA TCTACGGTAT TTGAATCTCT CTTCTACTGA
CATTAACAGG TTGCCAGAAT CATTGTGCAA CTTGTATAAT CTACGAACAT TAATATTGTA CGGATGTACT AAGTTGACCA
TGTTGCCGAT TAACATGCAC AATCTTGTGA ATTTACGGCA TCTTGATATT AGGAAAACTT GTTTGGAAGA AATGCCTGGA
GGAATAAGCA AAATGAAACA CTTGCATACC TTAAGTTCCT TTGTGGTGGG GAAGCGTGAA GATAATGGAA TCAAGGAATT
AGGAGGGCTC TCAAATCTTC ATGGATCACT TGAGCTTAAG AAGTTGGAGA ATATTGTTGA TGTGAAAGAA GCAGAGAATG
CAAGGATGAC AAACAAGAAT CTCATCAACG AATTATACTT GGAGTGGTCT TCAGGCGATG ATATGGTTCC GAACACAAAA
GCCGAAAGAG ATATACTCGA TAGCTTGCAA CCTCACAACA GCTTGAAAGA GTTGACAATC AAAGGATACA AGGGTACAAT
ATTTCCAGAT TGGTTGGGGA ACTGTTCATA CAACAATATG ACAAGTGTAT CTCTGGAGTC TTGCAACAAT TGCTGCATGC
TGCCTTCACT TGGACAGTTG CCATCTCTTA AGGCCCTGCG CATTAAAGGT TTTGGTCAGC TGAAGTGTGT TGACATGGAG
TTTTACAAGG GTATTTGTGA CCCTTCTTTG CATATTGCTC CTCCTTTTCC TTTGTTGGAG AGTTTGGAAT TTGATAACTT
GCCATGTTGG GAGGAGTGGC ACTTACCTGA CTCAAAAGTT TTTCCTCAGC TTAAGAGTCT TGAAATAGGA GATTGTCGAA
TGTTAAAGGG AGATATGCTT CATCAGGTAT TCATGAGATT TGTTTCTTCT TCGTCGGATG CTTTGAAAGT TCGCAAGCTA
GTTATCCAAT CTCTAAGAGC AGGGTTTGCA GATATGTCAC TTAAAGGGGA TAAATTATCA ATTAGGGCAT GTGAATCTGT
GGTGGAGTCT GCATTTAACG AAATGATCGG CATTAACCAT CTACCCTCCC TCCAAAAAAT AGAAATCTTG GGGTGTTCAT
TTGCTGTGTC CTGGCCGGAC AATTGTTTAT TACCCAAATG TTTGCAAAAG CTCGCAATCC GGCAATGCAG AAAACTGGAA
TTCCTGGACC AGAAGTATGA TTTGGTAAAG CTACAAATAG AAGACAGTTG TGATTCACTG ACCTCCTTGT CGTTGGATGT
CTTTCCCAAT CTCAAGAATC TCGAGATAAT AGGGTGTAGG AATCTGGAAT CAGTGTCAAT GTCAGAGGCA CCACACGCTG
CTCTTCAACG TCTCTCCATT AGTTTCTGCG AGAAATTAGT GTCATTTGCA GGAGAAGGAC TGGCTGCACC CAACTTGACT
CATCTTCAAG TCAAAGGGTG CTGGAAGTTG GAGGCATTAC CACGTGACAT GAAGAGTCTA CTCCCAAGTC TACAGTCTCT
CAAGATATCT GGTTGCTCTG ACATGTGCAG GTTGGCAGAG GGTGATTTGC CGCCTAACTT GAAATCACTT TATGTGGGAA
```

FIG. 1

```
TTTGCGAGCA ACAAATTAGG GATCTATCGT GGATGGGCAA TTTGGACGCC CTCACTCATC TTACACTTTA TGGTTATAAG
TGTAAGAACA TAAAGTCATA CCCAGAGGTG GGTTCGCTGC CTCACCTTCC CTCCCTTACC ACTCTTGTGA TATTGCACTT
CCGTAATCTG GAGACATTGG AGTGCAACGA GCTTCTCCGC CTCACCTCCC TTCAACAACT ATACATTGGT TGGTGTCCAA
AGCTGGAGAA TATGGAAGGA GAAAAGCTGC CTCCCTCTCT CTTGCTACTT GACGTTTATA GTTGTGGTTT GCTGGAAGAA
CACTGCAAGA ACAAGCATCA ACTAATCTGG CCCAAAATTT CCCACATCCC CACCATTCAA GTCAATGGCA AGAAACTTTC
CTGAATAGAG ATTTCTGAGC AGGTAAATCT CTAATCTTCA TGTTTCTCAT GCTAAATTGA CACACGCATA AATTTCCATT
TCCTTCAGGA GAAAAATAAT TCTATCTTTC TTTGACAATT GAAATCGTAT GCCAAATTGC AATCTTTTCT TTCATTTATC
TGGGAAGCTC AAACTTTGCA GTTGTAGTTA AAGAAATATC TTTTGTTTCT TTCACAAACT CATTGCTCTC TCTAATACTT
ATTAACATTC ATATTTTTCA ATAAAGACAG TGACTATCTT TTGTGTGTAT CCAACATTTA AGAATTTTTT TAGATGTATT
AAACAAAGAG TTTGGTTTAC CCGGTCATCC AATTAGATTC ATGCATTTAG ATGACTTTTG AAGTGATGAG TTTGAAACTT
AGTTACTTTA GTGGATTTAA GAATTATTTG TTGTGTACCT GAAGCTGTGC TTACAAAGTT CGGATACCAA AGGAAGACAT
CATGGAGAAA GTTGGAATGG CACTTCTTAT TGAAAAGATT CTTTTTTTTG TTGCTATGTT TCTCTTTTCC TCTATATAAT
TTTATTTTTG CTGTTTTGCA CAGAAAAAAA ATCAAATAAT AGCTTGATTT GTGGAAAGAA AAGAGTTATA AAATGGTATG
TGCAGTTTGT ACATATATTA ACCTGCAGTG GGATTCAAAT GATTTAAGAA AAAGAATTGT CATAGAATAT TTGATCGTTT
TGGACTGAAT TGAAGAGGAT AGCTACAAAT ATACAGGGTT ATTTTTATGC AAAGTCAGTG TATTATGTGT ATGGAAAAAT
TTTTCCTTTT ATAGCTTGTA GTATTATAAC CATCATCACT TTAGTTTCTT TATAATTGCT CTAGTTCTGT TTTGACTTCC
TGTTTTTGGG TGTCATTTCT TTTCTCAAAC CAATAATCCA ACATTGTGTT AATGAGGTTT TCACATAAGT GTGTCTGTGG
TTATTGTGAT GACATTATGA CAAACATTTA GTTTTGAAAT TTATATATAT ATAATTTGTG TTTCAGGAAA TACTTTGAAG
ATCAAGCAGC AATTGTCCTG AGAGCATTGC AGTTCTGGCT GGAATGGATC TTGAATGCCA GTTTCAGTCA AAACAAGCAA
AAGAAATGAA GAATCATTTT CCACCTTTAC TTTTGTTTTT CCAAAGAAAA AATAAGATTG AAAGATAACG GATGCCATTA
TGAAAATTAG TAATAGCACA TGGGTAGAAG AGATGATAAA GTTGCTATTA GAATGAAGGA GCATAACAGG TGAAGGAGTT
GTAAATATCA ATTCACATCA AATCATAGCT TTTCTTTTTC TTTTTATTTG TATATTTCTT TGATGTTTTA TCGTTGATAT
CCAATGCATG AATACATGAG TTCAAT
```

(SEQ ID NO: 1)

FIG. 1 CONTINUED

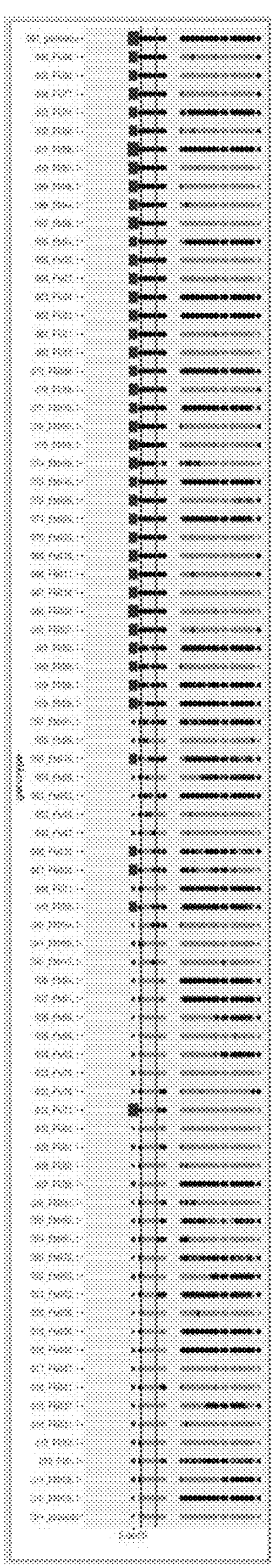
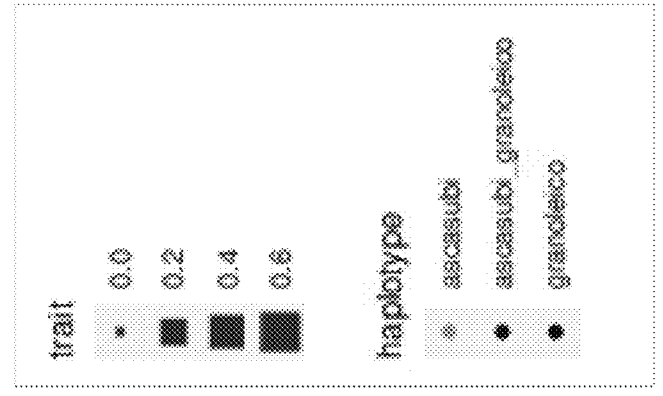
FIG. 3

SEQUENCE LISTING

```
Sequence total quantity: 4
SEQ ID NO: 1            moltype = DNA  length = 5066
FEATURE                 Location/Qualifiers
source                  1..5066
                        mol_type = genomic DNA
                        organism = Arachis hypogaea
SEQUENCE: 1
atggctggag ttcttgttgg tggagctttt ctgtctggct tcattaatgt tgtccttgac  60
aggctcattt ctgctgatgc tgtcaacttg gttgtgggta agaagcttag ctctgacttg  120
gttgagaggc tgaggaatgc tctgacagat gctggagatc ttgttgatga tgcagagttc  180
aagcaactgg ataaccatga tgtgaaggag tggctcaact ctctccgtga tgctctttac  240
actgctgatg acttgctgga ccgcgtctgc accaaagccg caactcaaaa ggtcactctc  300
ttgggtagaa tcttcaactc tgaagatagg cagatggtga atgagataga aagggtggtt  360
agaaggatag aagatcttga gaaccgcaaa ggaaagcttg ggcttgaaaa gatttccact  420
gctagcttct cctggaaaac tccatccact tctcttgtaa aagggaatgt gtgtggcagg  480
gaggatgaca agaaggcctt aatcaagatg ctgaatgaca acaatgagca tcacctctct  540
gtcatctcta ttgttggcat gggtggtgtt ggtaaaacta ctttagctca atggatgtac  600
aataatgcag agttgatgga gggatttgat cagaaagcat gggtttgtgt ttcggaaaac  660
ttcaatattg ttgagactac aaggaatata gtaaagcaga tctctacaaa tactcaggat  720
cttgatagct tcaattcaat tcaagatgct ttgaagaaag gattgtccga aaagaagttc  780
```

-continued

```
tttattgttg tggatgatgt ttggagcaat gatcatcatc aatggaagga ttttctagcc  840
ccttttcaat atggggttaa gggaagtact attcttctga ctactcgcaa ggtagatgtt  900
ggttcagttg ttcaaacaaa ttatcaacct cactatctca ttccattatc agaagactac  960
tgttggtcag tatttgcagc caatgcttct tttccagaat caaatgggaa cccgacacta  1020
gaaggaatag gcagaagcat tgctaggaag tgtgatggtt tgccattagc agccgaaacc  1080
cttggttgct tgtgcagaag gcatgatgct aaggaatggg aaaaaatctt aaggagtgat  1140
atttggggat tttctacaaa tgacagtaag attgttccag cattgttaat tagttacttt  1200
caccttgctg cacatttgaa gcgttgtttt gttcattgtg cactgtttcc aaaagattat  1260
cactttaaga aagatgaact aattttgttg tggatggccg aagatctttt aagactacca  1320
aagagaggag agagcttgga agaggttggt tgcaagtgtt ttgaagaatt agtttcaagg  1380
ttattcttta aaaagcttca agacgatgat gagtattttg tgatgcatga tctcttgcat  1440
gacttggcaa tattccttgc tggagatttc tattgtagaa tagaagaact tggtgaacaa  1500
gaggaaaaga tggttctcac tcgccatttg tcatatttgc cacctggaag gttagatcat  1560
ccaatctcaa aagtctttaa ctccaacgcg aggctggaat ctttcaggac atcgttgtat  1620
atcgatgatt tattcagcat ggaaagtgta gcatctaagt ttatatgcat gagagtttta  1680
tcctttcata aacttgatgt attacctgat tcaataggtg aatcgattca tctacggtat  1740
ttgaatctct cttctactga cattaacagg ttgccagaat cattgtgcaa cttgtataat  1800
ctacgaacat taatattgta cggatgtact aagttgacca tgttgccgat taacatgcac  1860
aatcttgtga atttacggca tcttgatatt aggaaaactt gtttggaaga aatgcctgga  1920
ggaataagca aaatgaaaca cttgcatacc ttaagttcct ttgtggtggg gaagcgtgaa  1980
gataatggaa tcaaggaatt aggagggctc tcaaatcttc atggatcact tgagcttaag  2040
aagttggaga atattgttga tgtgaaagaa gcagagaatg caaggatgac aaacaagaat  2100
ctcatcaacg aattatactt ggagtggtct tcaggcgatg atatggttcc gaacacaaaa  2160
gccgaaagag atatactcga tagcttgcaa cctcacaaca gcttgaaaga gttgacaatc  2220
aaaggataca agggtacaat atttccagat tggttgggga actgttcata caacaatatg  2280
acaagtgtat ctctggagtc ttgcaacaat tgctgcatgc tgccttcact tggacagttg  2340
ccatctctta aggccctgcg cattaaaggt tttggtcagc tgaagtgtgt tgacatggag  2400
ttttacaagg gtatttgtga cccttctttg catattgctc ctccttttcc tttgttggag  2460
agtttggaat ttgataactt gccatgttgg gaggagtggc acttacctga ctcaaaagtt  2520
tttcctcagc ttaagagtct tgaaatagga gattgtcgaa tgttaaaggg agatatgctt  2580
catcaggtat tcatgagatt tgtttcttct tcgtcggatg ctttgaaagt tcgcaagcta  2640
gttatccaat ctctaagagc agggtttgca gatatgtcac ttaaagggga taaattatca  2700
attagggcat gtgaatctgt ggtggagtct gcatttaacg aaatgatcgg cattaaccat  2760
ctaccctccc tccaaaaaat agaaatcttg ggtgtgttcat ttgctgtgtc ctggccggac  2820
aattgtttat tacccaaatg tttgcaaaag ctcgcaatcc ggcaatgcag aaaactggaa  2880
ttcctggacc agaagtatga tttggtaaag ctacaaatag aagacagttg tgattcactg  2940
acctccttgt cgttggatgt ctttcccaat ctcaagaatc tcgagataat agggtgtagg  3000
aatctggaat cagtgtcaat gtcagaggca ccacacgctg ctcttcaacg tctctccatt  3060
agtttctgcg agaaattagt gtcatttgca ggagaaggac tggctgcacc caacttgact  3120
catcttcaag tcaaagggtg ctggaagttg gaggcattac cacgtgacat gaagagtcta  3180
ctcccaagtc tacagtctct caagatatct ggttgctctg acatgtgcag gttggcagag  3240
ggtgatttgc cgcctaactt gaaatcactt tatgtgggaa tttgcgagca acaaattagg  3300
gatctatcgt ggatgggcaa tttggacgcc ctcactcatc ttacacttta tggttataag  3360
tgtaagaaca taaagtcata cccagaggtg ggttcgctgc ctcaccttcc ctcccttacc  3420
actcttgtga tattgcactt ccgtaatctg gagacattgg agtgcaacga gcttctccgc  3480
ctcacctccc ttcaacaact atacattggt tggtgtccaa agctggagaa tatggaagga  3540
gaaaagctgc ctccctctct cttgctactt gacgtttata gttgtggttt gctggaagaa  3600
cactgcaaga acaagcatca actaatctgg cccaaaattt ccccacatcc caccattcaa  3660
gtcaatggca agaaactttc ctgaatagag atttctgagc aggtaaatct ctaatcttca  3720
tgtttctcat gctaaattga cacacgcata aatttccatt tccttcagga gaaaaataat  3780
tctatctttc tttgacaatt gaaatcgtat gccaaattgc aatcttttct ttcatttatc  3840
tgggaagctc aaactttgca gttgtagtta aagaaatatc ttttgtttct ttcacaaact  3900
cattgctctc tctaatactt attaacattc atatttttca ataaagacag tgactatctt  3960
ttgtgtgtat ccaacattta agaatttttt tagatgtatt aaacaaagag tttggtttac  4020
ccggtcatcc aattagattc atgcatttag atgacttttg aagtgatgag tttgaaactt  4080
agttacttta gtggatttaa gaattatttg ttgtgtacct gaagctgtgc ttacaaagtt  4140
cggataccaa aggaagacat catggagaaa gttggaatgg cacttcttat tgaaaagatt  4200
cttttttttg ttgctatgtt tctcttttcc tctatataat tttatttttg ctgttttgca  4260
cagaaaaaaa atcaaataat agcttgattt gtggaaagaa aagagttata aaatggtatg  4320
tgcagtttgt acatatatta acctgcagtg ggattcaaat gatttaagaa aaagaattgt  4380
catagaatat ttgatcgttt tggactgaat tgaagaggat agctacaaat atacagggtt  4440
atttttatgc aaagtcagtg tattatgtgt atggaaaaat tttccttttt atagcttgta  4500
gtattataac catcatcact ttagtttctt tataattgct ctagttctgt tttgacttcc  4560
tgtttttggg tgtcatttct tttctcaaac caataatcca acattgtgtt aatgaggttt  4620
tcacataagt gtgtctgtgg ttattgtgat gacattatga caaacattta gttttgaaat  4680
ttatatatat ataatttgtg tttcaggaaa tactttgaag atcaagcagc aattgtcctg  4740
agagcattgc agttctggct ggaatggatc ttgaatgcca gtttcagtca aaacaagcaa  4800
aagaaatgaa gaatcatttt ccacctttac ttttgttttt ccaaagaaaa aataagattg  4860
aaagataacg gatgccatta tgaaaattag taatagcaca tgggtagaag agatgataaa  4920
gttgctatta gaatgaagga gcataacagg tgaaggagtt gtaaatatca attcacatca  4980
aatcatagct ttctttttc tttttatttg tatatttctt tgatgtttta tcgttgatat  5040
ccaatgcatg aatacatgag ttcaat                                      5066
```

```
SEQ ID NO: 2           moltype = DNA  length = 177
FEATURE                Location/Qualifiers
source                 1..177
                       mol_type = genomic DNA
                       organism = Arachis hypogaea
SEQUENCE: 2
```

-continued

```
tccaccaaca agaactccag ccatgatctc aaacaagatc aaagtattca aattttaaga  60
atagaaggaa agaaatatgc ttaaagtttc cagaatagaa ggaaagaaca attctttgca  120
attgcaagtt aggaacaaga cgtggtatta atctctgaga taacttaatt taaaaca     177

SEQ ID NO: 3           moltype = DNA  length = 202
FEATURE                Location/Qualifiers
source                 1..202
                       mol_type = genomic DNA
                       organism = Arachis hypogaea
SEQUENCE: 3
tggagtaact tttcattttt ataacactac tttaaatgtt attgtcattt tggaaggtgc  60
accgtaattg cataaaacct ttaatgttta atcatattcc tactttttga aagatgcaat  120
gagatttcaa gatgtataaa gttcaaactt tttttaggac caatggaaat gtagtcttta  180
tcagaaagaa tctgaataat tt                                           202

SEQ ID NO: 4           moltype = DNA  length = 380
FEATURE                Location/Qualifiers
misc_feature           1..380
                       note = Smut-Resistant Gene Variant
source                 1..380
                       mol_type = other DNA
                       organism = synthetic construct
SEQUENCE: 4
tccaccaaca agaactccag ccatgatctc aaacaagatc aaagtattca aattttaaga  60
atagaaggaa agaaatatgc ttaaagtttc cagaatagaa ggaaagaaca attctttgca  120
attgcaagtt aggaacaaga cgtggtatta atctctgaga taacttaatt taaaacaatg  180
gagtaacttt tcatttttat aacactactt taaatgttat tgtcattttg gaaggtgcac  240
cgtaattgca taaaaccttt aatgtttaat catattccta ctttttgaaa gatgcaatga  300
gatttcaaga tgtataaagt tcaaactttt tttaggacca atggaaatgt agtctttatc  360
agaaagaatc tgaataattt                                              380
```

METHODS AND ASSAYS FOR IDENTIFYING, CREATING, AND CULTIVATING DISEASE-RESISTANT PEANUT LINES

CROSS REFERENCE TO RELATED APPLICATIONS

This application claims the benefit of and priority to U.S. Provisional Application No. 63/530,941, filed on Aug. 4, 2023, and entitled "Methods and Assays for Identifying, Creating, and Cultivating Disease-Resistant Peanut Lines," the disclosure of which is expressly incorporated by reference in its entirety.

SEQUENCE LISTING

The material in the accompanying sequence listing is hereby incorporated by reference in its entirety into this application. The accompanying file, named 00H670_401072_sequence_listing_tobefiled.xml, is 10.5 KB and was created on Jul. 31, 2024.

FIELD OF THE DISCLOSURE

The present disclosure relates generally to methods of detecting a smut-resistant gene variant in a peanut plant and using the smut-resistant gene variant to identify, create, and cultivate peanut lines that are resistant to peanut smut.

BACKGROUND

Peanut smut is a soilborne disease caused by the fungus, *Thecaphora frezii*, and is an emerging threat to worldwide peanut production. The spores of the fungus infiltrate the pod, most likely during pegging, and replace developing seeds. The disease causes hypertrophy of pod tissues and seeds colonized with teliospores have a smutted mass appearance. Spores of the fungus are dispersed when pods are disrupted by shelling and easily spread by wind and weather events. Unfortunately, symptoms of peanut smut infection are not observable above ground.

Most commercial cultivars in South America are highly susceptible to this disease. For instance, smut infestation has been found in 100 percent of Argentinian peanut growing regions and has been reported in Brazil and Bolivia in wild type species. Smut infestation can result in substantial yield productions. In fact, the USDA APHIS restricts importation of peanuts from Argentina and Brazil for planting and places restrictions on importation of raw peanuts to the United States for other uses due to the risk of peanut smut infestation.

Cultural management strategies and chemical treatment have not been effective. Management of smut by fungicide application is variable and host plant resistance is the most sustainable method for disease control. While resistance to peanut smut has been discovered among *Arachis* wild species (Bressano et al., 2019; de Blas et al., 2019) and in the INTA and USDA germplasm collection (Wann et al., 2020), screening for smut-resistant germplasm requires years of field trials and is currently the only option for breeders since genetic markers for resistance have not yet been developed. As such, peanut smut continues to constitute a threat to the peanut industry around the world.

Accordingly, there remains a need in the art to identify a gene variant that confers immunity to peanut smut and for methods to detect and identify the gene variant for peanut smut resistance.

SUMMARY

The problems expounded above, as well as others, are addressed by the following inventions, although it is to be understood that not every embodiment of the inventions described herein will address each of the problems described above.

In some embodiments, a method of identifying a peanut line that is resistant to peanut smut is provided, the method including obtaining a biological sample from at least one peanut in the peanut line; performing whole genome sequencing on at least a portion of the biological sample to generate at least one target sequence; comparing the at least one target sequence to a peanut reference sequence, wherein the peanut reference sequence includes SEQ ID NO. 4; and identifying the peanut line as being resistant to peanut smut if the at least one target sequence comprises at least 98 percent identity to the peanut reference sequence.

In one embodiment, the method may further include identifying the peanut line as being resistant to peanut smut if the at least one target sequence is identical to the peanut reference sequence. In another embodiment, the method may further include identifying the peanut line as being resistant to peanut smut if a single nucleotide polymorphism (SNP) is detected in the biological sample at position 2490326 of chromosome 12 of the target sequence. In still another embodiment, the SNP includes a substitution of an adenine for a guanine. In yet another embodiment, the peanut line is resistant to peanut smut caused by colonization of *Thecaphora frezzii*. In some embodiments, the peanut line is a recombinant inbred line of peanuts.

In further embodiments, a method of producing a smut resistant peanut plant or a part thereof is provided, the method including crossing a peanut plant having a resistance allele associated with smut resistance with itself or a second peanut plant, wherein the resistance allele includes a single nucleotide polymorphism (SNP) at position 2490326 of chromosome 12 and the SNP includes a substitution of an adenine for a guanine; harvesting a resulting peanut seed; and growing the peanut seed to produce the smut resistant peanut plant or part thereof. In one embodiment, the peanut plant is obtained from a recombinant inbred line of peanuts. In another embodiment, the smut resistant peanut plant is resistant to peanut smut caused by colonization of *Thecaphora frezzii*. In still another embodiment, the method may include employing the smut resistant peanut plant as a source of breeding material. In another embodiment, a smut-resistant peanut plant or part thereof produced according to the method described above is provided.

In still further embodiments, a method of treating or preventing peanut smut infestation in a geographic region in need thereof is provided, the method including identifying a line of smut resistant peanuts, wherein at least one peanut from the line includes a single nucleotide polymorphism (SNP) at position 2490326 of chromosome 12 of its genome, wherein the SNP includes a substitution of an adenine for a guanine; and cultivating the identified line of smut-resistant peanuts in the geographic region. In one embodiment, the line is obtained from a recombinant inbred line of peanuts. In another embodiment, the identified line of smut-resistant peanuts is resistant to peanut smut caused by colonization of *Thecaphora frezzii*. In still another embodiment, the cultivating step further includes growing the identified line of smut-resistant peanuts under plant growth conditions.

BRIEF DESCRIPTION OF THE DRAWINGS

Further features and advantages can be ascertained from the following detailed description that is provided in connection with the drawings described below:

FIG. 1 is a sequence of a resistance gene retrieved from the *Arachis hypogaea* (peanut) genome according to one embodiment.

FIG. 3 is a graphical representation showing the results of screening and sorting the RIL peanut populations for the contribution of smut-resistant variety haplotypes in QTL region and smut-susceptible variety haplotypes for the genome background.

DETAILED DESCRIPTION

Figure 2:
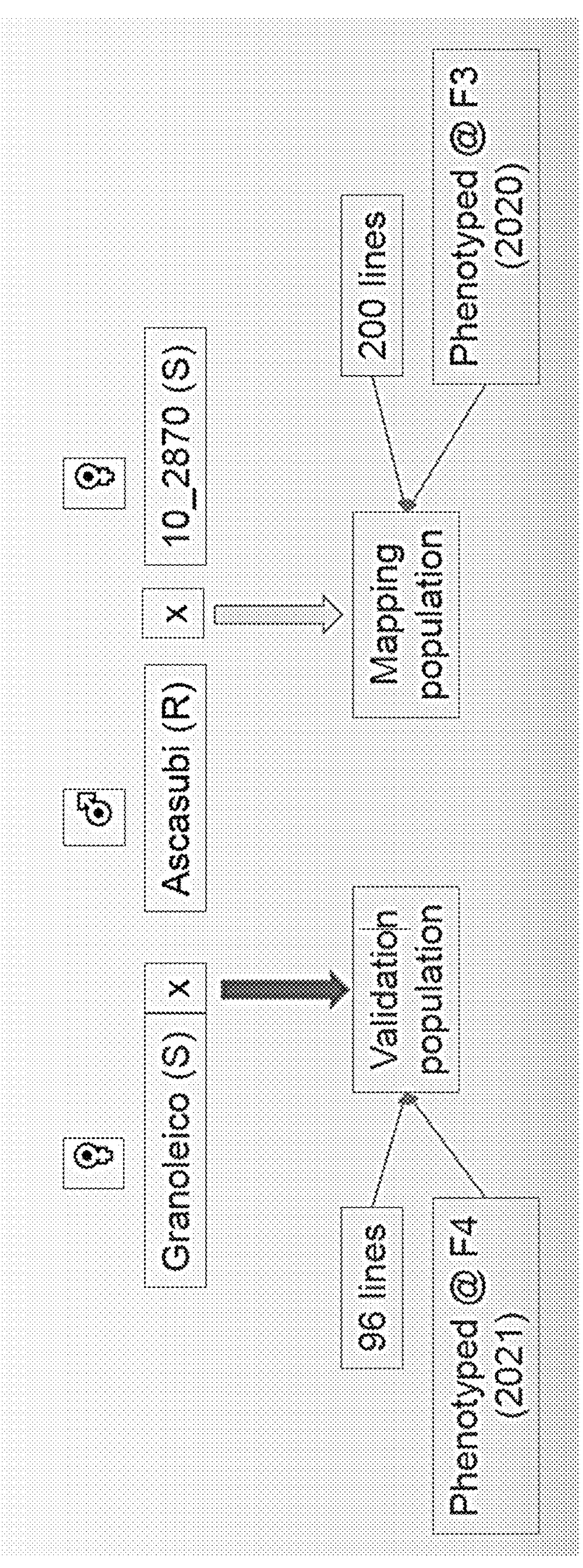
FIG. 2 is a graphical representation showing two recombinant inbred line (RIL) peanut populations for determining a resistance gene cluster associated with smut resistance in peanuts.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity. All patents, patent applications, published applications and publications, GenBank sequences, databases, websites and other published materials referred to throughout the entire disclosure herein, unless noted otherwise, are incorporated by reference in their entirety.

In certain instances, nucleotides and polypeptides disclosed herein are included in publicly available databases, such as GENBANK® and SWISSPROT. Information including sequences and other information related to such nucleotides and polypeptides included in such publicly available databases are expressly incorporated by reference. Unless otherwise indicated or apparent, the references to such publicly available databases are references to the most recent version of the database as of the filing date of this Application.

Following long-standing patent law convention, the terms "a", "an", and "the" refer to "one or more" when used in this application, including the claims. Thus, for example, reference to "a cell" includes a plurality of such cells, and so forth.

The term "substantially" allows for deviations from the descriptor that do not negatively impact the intended purpose. Descriptive terms are understood to be modified by the term "substantially" even if the word "substantially" is not explicitly recited.

The terms "comprising," "including," "having," and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc.

The terms "about" and "approximately" shall generally mean an acceptable degree of error or variation for the quantity measured given the nature or precision of the measurements. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

For the purposes of the present disclosure, the term "gene" has its meaning as understood in the art. However, it will be appreciated by those of ordinary skill in the art that the term "gene" has a variety of meanings in the art, some of which include gene regulatory sequences (e.g., promoters, enhancers, etc.) and/or intron sequences, and others of which are limited to coding sequences. As used herein, the term "gene" can generally refer to a portion of a nucleic acid that encodes a protein. The term can optionally encompass regulatory sequences. The word "gene" can also include references to nucleic acids that do not encode proteins but rather encode functional RNA molecules such as transfer RNAs (tRNAs), ribosomal RNAs (rRNAs), small RNAs (including, but not limited to microRNAs, siRNAs, piRNAs, snoRNAs, snRNAs, cxRNAs, scaRNAs) and the long non-coding RNAs. For the purpose of clarity, as used in the present application, the term "gene" generally refers to a portion of a nucleic acid that encodes a protein. This definition is not intended to exclude application of the term "gene" to non-protein coding expression units but rather to clarify that, in most cases, the term as used herein refers to a protein coding nucleic acid.

A gene product or expression product is, in general, an RNA transcribed from the gene or a polypeptide encoded by an RNA transcribed from the gene. Expression of a gene can be measured by a variety of techniques known in the art. Certain techniques can make use of a polynucleotides corresponding to part or all the gene rather than an antibody that binds to a polypeptide encoded by the gene. Appropriate techniques include, but are not limited to, in situ hybridization, Northern blot, and various nucleic acid amplification techniques such as PCR, quantitative PCR, and the ligase chain reaction.

The term, "allele," refers to any of one or more alternative forms of a gene locus, all of which alleles relate to one trait or characteristic.

The term, "genotype," refers to the genetic constitution of a cell or organism.

The term, "haplotype," refers to the set, made up of one allele of each gene, including the genotype. The term can also be used to refer to the set of alleles on one chromosome or a part of a chromosome, for example, one set of alleles of linked genes.

The term, "phenotype," refers to the detectable characteristics of a cell or organism, which characteristics are the manifestation of gene expression. For example, the phenotype of a plant refers to the observable characteristics of a plant, such as its height, leaf shape, or biomass.

The term, "Quantitative Trait Loci," refers to genetic loci that control to some degree, numerically representable traits that are usually continuously distributed.

The present disclosure provides methods and kits for detecting gene variants and identifying peanut lines that are resistant to fungal disease. In some embodiments, the methods and kits of the present disclosure are able to detect gene variants and identify peanut lines that are resistant to peanut smut, which is a disease caused by the fungus, *Thecaphora frezzii*. *Thecaphora frezzii* is a biotrophic obligate parasite of peanut plants. An infected peanut's pod generally will have hypertrophic cells in the form of galls and a spongy consistency. The cells of the grains inside the pods are destroyed and replaced by reddish-brown teliospores. This causes a partial or total destruction of the peanut fruit. By utilizing the gene variants described herein and the methods of the present disclosure, peanut lines can be selected for resistance to peanut smut at the seedling or seed stage, which offsets the need to grow the peanut lines for a full field season and spend the labor and time to phenotype each line to determine resistance.

In one embodiment, the present disclosure provides methods for detecting a gene variant in a peanut plant that is responsible for resistance to peanut smut. As used herein, "resistance" refers to the intrinsic ability of a plant to prevent infection of disease. In this aspect, to detect a gene variant or biomarker specific for peanut smut resistance, the method may include breeding two or more recombinant inbred line (RIL) peanut populations comprised of a peanut smut resistant strain and a peanut smut susceptible strain. "Recombinant inbred lines" (RILs) are a collection of strains that can be used to map quantitative trait loci. Parent strains are crossed to create recombinants that are then inbred to isogenicity, resulting in a resource for trait mapping and analysis. In some embodiments, the RIL populations and their parental lines can be phenotyped to determine incidence of peanut smut disease and sequenced to determine the genotype. Analysis of the phenotypic and genotypic data can be used to determine a quantitative trait locus (QTL). In one embodiment, the phenotypic and genotypic data can be analyzed using the computational tool, Khufu, which was developed by the Applicant, HudsonAlpha Institute for Biotechnology.

In one embodiment, the analysis performed by the detection algorithm results in the identification of the quantitative trait locus (QTL). A QTL is a region of DNA associated with a specific phenotype or trait that varies within a population. QTLs are mapped by identifying molecular markers that correlate with a trait. QTL analysis is a statistical method that links phenotypic traits to genotypic data to explain the genetic basis of complex traits. In one embodiment of the present disclosure, a QTL associated with smut resistance can be identified.

Within the QTL region identified by the methods of the present disclosure, the inventors surprisingly discovered a resistance gene ("R-gene") having a single nucleotide variant that is associated with peanut smut resistance. The sequence of the R-gene retrieved from the *Arachis hypogaea* (peanut) genome is shown in FIG. 1 as SEQ ID NO: 1 (available from PeanutBase. Table 1 below shows the exemplary single nucleotide variant for peanut smut resistance.

TABLE 1

Exemplary Gene Variant for Peanut Smut Resistance

| Chromosome | Position | Resistance Allele | Wild Type Allele | Left Flank | Right Flank | Sequence |
|---|---|---|---|---|---|---|
| 12 | 2490326 | A | G | TCCACCAACAA GAACTCCAGCC ATGATCTCAA ACAAGATCAAA GTATTCAAATT TTAAGAATA GAAGGAAAGA AATATGCTTAA AGTTTCCAGA ATAGAAGGAAA GAACAATTCTT TGCAATTGC AAGTTAGGAAC AAGACGTGGTA TTAATCTCT GAGATAACTTA ATTTAAAACA (SEQ ID NO: 2) | TGGAGTAACTT TTCATTTTTAT AACACTACTTT AAATGTTATTG TCATTTTGGAA GGTGCACCGT AATTGCATAA AACCTTTAATG TTTAATCATAT TCCTACTTTTT GAAAGATGCA ATGAGATTTCA AGATGTATAA AGTTCAAACTT TTTTTAGGACC AATGGAAATG TAGTCTTTATC AGAAAGAATC TGAATAATTT (SEQ ID NO: 3) | TCCACCAACAAGA ACTCCAGCCATGA TCTCAAACAAGAT CAAAGTATTCAAA TTTTAAGAATAGA AGGAAAGAAATAT GCTTAAAGTTTCC AGAATAGAAGGA AAGAACAATTCTT TGCAATTGCAAGT TAGGAACAAGACG TGGTATTAATCTCT GAGATAACTTAAT TTAAAACAATGGA GTAACTTTTCATTT TTATAACACTACT TTAAATGTTATTGT CATTTTGGAAGGT GCACCGTAATTGC ATAAAACCTTTAA TGTTTAATCATATT CCTACTTTTTGAA AGATGCAATGAGA TTTCAAGATGTAT AAAGTTCAAACTT TTTTTAGGACCAA TGGAAATGTAGTC TTTATCAGAAAGA ATCTGAATAATTT (SEQ ID NO: 4) |

As can be seen in Table 1 and SEQ ID NO: 1 of FIG. 1, in various embodiments, the gene variant associated with peanut smut resistance can be located on chromosome 12 of the peanut genome. In one embodiment, the gene variant that confers resistance to peanut smut in a peanut plant is located at position 2490326 of chromosome 12 of the peanut genome. In some embodiments, the gene variant can include a single nucleotide polymorphism (SNP). As used herein, a "single nucleotide polymorphism" (SNP) refers to a genomic variant at a single base position in a DNA sequence. As shown in Table 1, the SNP can be a substitution of an adenine for a guanine. In one embodiment, the gene variant that confers resistance to peanut smut in a peanut plant includes a substitution of an adenine in place of a guanine at position 2490326 of chromosome 12 of the peanut genome. In such an embodiment, the resistance allele includes an adenine at position 2490326 of chromosome 12 of the peanut genome.

The methods of the present disclosure can be used to detect the above-identified gene variant in peanut plants in order to identify both peanut lines that are suspected of being resistant to peanut smut and peanut lines that are susceptible to peanut smut infection. In this aspect, the methods include obtaining a biological sample from a peanut plant. A "biological sample," as used herein, refers to a sample of biological material obtained from a plant. In one embodiment, the plant is a peanut plant. Examples of a biological sample include a tissue sample, a cell sample, genetic material, or a combination thereof from a plant. "Biological sample" can refer to a sample of tissue or material isolated from the plant. In some embodiments, the biological sample is isolated from a peanut. Exemplary biological samples from a peanut include, but are not limited to, the seeds, the roots, the stem, the leaves, the flowers, the pegs, the pods, the pod shells, or a combination thereof. Non-limiting examples of the biological sample include, fresh plant matter, plant matter placed within an RNA stabilization reagent such as an RNA later solution, plant matter stored within silica gel, freeze-dried plant matter, plant matter stored in an ethanol solution, fresh frozen (FF) samples, formalin-fixed plant matter, formal-fixed paraffin-embedded (FFPE) plant matter, or other prepared sample types.

The biological sample can be obtained by a variety of conventional techniques. As used herein, the phrase, "obtaining a biological sample," refers to any process for directly or indirectly acquiring or generating the biological sample from the plant. For example, the biological sample can be obtained from the plant at any point in the supply chain. The biological sample can be obtained from a field, a factory, a farm, a peanut supplier, a laboratory facility, a manufacturer, a distributor, a retailer, or any other point in the supply chain. In another embodiment, a biological sample can be obtained by receiving the biological sample (for example, at a laboratory facility) from one or more persons who procured the sample directly or indirectly from the plant.

In some embodiments, the methods described herein involve obtaining a biological sample, such as plant matter, from a peanut suspected of being resistant to peanut smut. In this embodiment, the plant matter may contain at least one cell that is suspected of being resistant to peanut smut. In another embodiment, the methods described herein involve obtaining a biological sample, such as plant matter, from a peanut that is susceptible to peanut smut infection. In this aspect, the plant matter may be examined for reference markers that indicate peanut smut susceptibility. In still another embodiment, the biological sample may be obtained from a recombinant inbred line (RIL) of peanuts. In further embodiments, the biological sample may be obtained from a peanut line having a high oleic content. For example, the peanut line may include about 75 percent or more of oleic acid. In another embodiment, the peanut line may include about 80 percent or more of oleic acid.

The biological sample from the peanut plant can be examined for one or more biomarkers. In one embodiment, the biological sample can be examined for one or more biomarkers that indicate the plant, for example, the peanut plant, is resistant to peanut smut. For example, in this embodiment, the biomarker may include the resistance allele shown in Table 1 above. In another embodiment, the biological sample can be examined for one or more biomarkers that indicate the plant, for example, the peanut plant, is susceptible to peanut smut infection. For instance, the biomarker may include the wild type allele shown in Table 1 above. In certain embodiments, the biomarkers include genetic signatures that are uniquely present in different subgroups of plants, such as peanuts.

In one embodiment, whole genome sequencing is performed on at least a portion of the biological sample to generate at least one target sequence and analyze the presence or absence of biomarkers. Whole genome sequencing (WGS) is a technique that reads all of an organism's DNA. WGS generates enough sequence to read each letter, or base pair, of a target genome numerous times. For example, human genomes for clinical use are sequenced to an average depth of 30 reads per base pair. This "genome coverage," or the amount of sequence generated needed to cover a target genome x number of times, directly impacts the time and expense of reading the DNA of a single individual.

In some embodiments, the whole genome sequencing performed on the biological sample is low coverage. Low coverage whole genome sequencing, as described herein, refers to sequencing to about 5× coverage or less, and preferably about 1× coverage or less. For example, the biological sample can be sequenced at a depth of about 1× coverage or less. In addition, while whole genome sequencing has been described herein for generating one or more target sequence reads of the biological sample, other methodology for analyzing a large number of nucleic acids in a single reaction can be utilized. For instance, the methods may employ other high-throughput nucleic acid sequencing technologies, such as next generation sequencing (NGS). In one embodiment, a targeted RNA-sequence panel can be offered on an NGS platform. Non-limiting examples of such NGS technologies include instruments and protocols from Illumina, Inc (San Diego, CA, USA), Thermo Fischer Scientific (Waltham, MA, USA), Qiagen (Venlo, Netherlands).

In still other embodiments, certain multiplex PCR-based platforms are employed. Embodiments may use qPCR-based platforms configured to accommodate a substantial number of analytes, such as the Qiagen Modaplex (Venlo, Netherlands) or similar platform. Embodiments can also employ conventional real time PCR platforms. The term "PCR" or "polymerase chain reaction" as used herein refers to the use of template DNA, nucleotides (dNTPS) and primers that bind to the template DNA to selectively amplify a target sequence. PCR is a technology that can be used to amplify a single copy or few copies of a DNA sequence by several orders of magnitude, generating thousands to millions of copies of the DNA sequence. Standard PCR methods are known in the art. PCR amplification and the detection of an amplified target sequence can be used to detect specific gene elements in a sample. Quantitative PCR methods such as real time PCR may be used to determine the absolute or relative amounts of a known sequence in a sample. Digital PCR methods may also be used for detecting and/or quantifying target sequences in a sample.

In further embodiments, any of various expression microarray-based platforms can be utilized, including, but not limited to those from Affymetrix (Santa Clara, CA, USA), Aknonni Biosystems (Frederick, MD, USA), Biofire Diagnostics (Salt Lake City, UT, USA), or similar platforms. Some embodiments may employ non-array platforms and protocols. In certain non-array embodiments, a quantitative nuclease protection assay is utilized. Other non-array embodiments employ platforms and protocols from NanoString Technologies, Inc. (Seattle, WA, USA). The examples provided herein are merely exemplary and should not be considered limiting in any way. Embodiments employ any of various molecular diagnostic platforms.

Certain embodiments may employ a DNA chip, which is a device that is convenient to compare expression levels of a number of genes at the same time. DNA chip-based expression profiling can be carried out, for example, by the method as disclosed in "Microarray Biochip Technology" (Mark Schena, Eaton Publishing, 2000). A DNA chip comprises immobilized high-density probes to detect a number of genes. Thus, expression levels of many genes can be estimated at the same time by a single round analysis. Namely, the expression profile of a specimen can be determined with a DNA chip.

In some embodiments, after the target sequence(s) have been generated, the target sequence(s) can be compared to a reference genome. In one embodiment, the reference genome is obtained from a peanut known to be resistant to peanut smut. In this embodiment, the reference genome includes the resistance allele identified in Table 1 above, for example, the resistance allele including an adenine at position 2490326 of chromosome 12 of the peanut genome. In another embodiment, the reference genome may be obtained from a peanut known to be susceptible to peanut smut. In this embodiment, the reference genome may include the wild type allele identified in Table 1 above, for example, the wild type allele including a guanine at position 2490326 of chromosome 12 of the peanut genome.

A measurement, such as a level of similarity to the sequence of nucleotides in the reference genome, can be used to compare the target sequence(s) and the reference genome. If the target nucleotide sequence(s) vary from that of the reference genome, the target peanut plant may have an increased likelihood of being resistant to peanut smut, a decreased likelihood of being resistant to peanut smut, or a combination thereof. The phrase "vary from that of the reference genome" is understood as having a level of the marker to be detected that is statistically different than a sample from a wild type control or a genetic variant sample from a plant that is known to be resistant to peanut smut. Statistical methodology may be employed to determine an acceptable degree of variance. Determination of statistical significance is within the ability of those skilled in the art, for example, the number of standard deviations from the mean that constitute a positive or negative result.

In some embodiments, the target sequence read(s) can be determined to be substantially similar to that of the reference genome when the target sequence read(s) includes at least 90 percent identity to the reference genome. For example, the target sequence can be determined to be substantially similar to the reference sequence if the target sequence includes at least 90 percent identity to at least 10 consecutive nucleotide bases from the peanut reference sequence. In another embodiment, the target sequence read(s) can be determined to be substantially similar to that of the reference genome when the target sequence read(s) includes at least 95 percent identity to the reference genome. For instance, the target sequence can be determined to be substantially similar to the reference sequence if the target sequence includes at least 95 percent identity to at least 10 consecutive nucleotide bases from the peanut reference sequence. In still another embodiment, the target sequence read(s) can be determined to be substantially similar to that of the reference genome when the target sequence read(s) includes at least 98 percent identity to the reference genome. For example, the target sequence can be determined to be substantially similar to the reference sequence if the target sequence includes at least 98 percent identity to at least 10 consecutive nucleotide bases from the peanut reference sequence. In yet another embodiment, the target sequence read(s) can be determined to be substantially similar to that of the reference genome when the target sequence read(s) includes at least 99 percent identity to the reference genome. For instance, the target sequence can be determined to be substantially similar to the reference sequence if the target sequence includes at least 99 percent identity to at least 10 consecutive nucleotide bases from the peanut reference sequence. In another embodiment, the target sequence read(s) can be determined to be substantially similar to that of the reference genome when the target sequence read(s) are identical to the reference genome. In still another embodiment, the target sequence read(s) can be determined to be substantially similar to that of a reference genome from a peanut plant that is known to be resistant to peanut smut when the target sequence read(s) includes a SNP at position 2490326 of chromosome 12 of the peanut genome, where the SNP include a substitution of an adenine for a guanine.

By comparing the target sequence reads to the reference genome in accordance with the methods of the present disclosure, the presence or absence of the gene variant responsible for resistance to peanut smut can be determined. For instance, in one embodiment, the methods can predict the likelihood that the target peanut plant (and its peanut line) is resistant or susceptible to peanut smut infestation. In further embodiments, the methods also provide for the identification of distinct subgroups of peanuts based on the presence or amount of the disclosed gene variant in the biological sample. Non-limiting subgroups of peanuts include peanut-smut resistant peanuts and peanut smut susceptible peanuts. The disclosed genetic markers and methods described herein allow peanut breeders and farmers to identify and screen for smut-resistant peanut lines and breed peanut lines having a decreased likelihood of being susceptible to peanut smut infestation.

In some embodiments, the present disclosure provides methods of identifying a line of peanuts that are resistant to peanut smut infection. In one embodiment, the methods may include obtaining a biological sample from at least one peanut in the peanut line and performing whole genome sequencing on at least a portion of the biological sample to generate at least one target sequence. The peanut line can be identified as being resistant to peanut smut if the disclosed gene variant is present. For instance, the peanut line can be identified as being resistant to peanut smut if a SNP is detected in the biological sample at position 2490326 of chromosome 12 of the target sequence and the SNP is a substitution of an adenine for a guanine.

In further embodiments, the present disclosure provides methods of creating a line of peanuts that are resistant to peanut smut infection. In this embodiment, once a peanut or peanut line is identified as being resistant to peanut smut infection, the peanut or peanut line may be used to breed or create a population of peanuts that is resistant to peanut smut. Any plant breeding technique known in the art may be used to create the smut-resistant peanut(s). In one embodiment, the smut resistant peanut population can be created using marker-assisted breeding. Marker-assisted breeding (MAB) uses DNA markers to identify plants with desirable traits early in their development, which can reduce the time it takes to find varieties with those traits. In another embodiment, the smut resistant peanut population can be created using speed breeding. Speed breeding (SB) is a technology to develop new varieties of plants in a shorter time, utilizing the manipulation of controlled environmental conditions.

In some embodiments, a method for hybridizing a resistance gene from an allele in peanuts that contributes to resistance to peanut smut is provided. In this embodiment, the method includes hybridizing a probe to the resistance gene isolated or derived from a target peanut; and detecting the presence of a hybridization product by measuring conformational changes in the probe that are indicative of hybridization to the resistance gene. In one embodiment, the probe includes a sequence that is complementary to the sequence of the gene variant with the resistance allele identified in Table 1. In another embodiment, the resistance gene includes the SNP described above as compared to a gene that is isolated from a control peanut plant at the same allele as the resistance allele, wherein the control peanut plant is susceptible to peanut smut.

In still further embodiments, a method for preventing, treating, or ceasing peanut smut infection in a peanut crop in need thereof is provided. The phrase, "preventing, treating, or ceasing peanut smut," and similar phrases as used herein, can refer to partially or totally inhibiting, delaying, or preventing the progression of peanut smut in a given geographic area; partially or totally inhibiting, delaying, or preventing the recurrence of peanut smut in a given geographic area; or preventing the onset or development of peanut smut in a given geographical area. Preventing, treating, or ceasing peanut smut can be indicated by stopping or reducing the incidence proliferation of peanut smut disease in a given geographic area. In this embodiment, the method may include identifying a strain of peanuts that is resistant to peanut smut and cultivating the identified smut-resistant strain of peanuts. In some embodiments, the identified smut-resistant strain of peanuts is cultivated in a region that is known to be infected with peanut smut or a region that is susceptible to infection with peanut smut. For example, the identified smut-resistant strain of peanuts can be grown under conditions conducive to plant growth.

In some embodiments, the present disclosure also provides a method of predicting the amount of peanut crop produced from a given peanut line. The method may include detecting the one or more gene variants as described herein and determining the likelihood of whether the peanut crop is susceptible to infestation of peanut smut (and hence plant death).

In still further embodiments, the present disclosure provides for peanuts that include the gene variant disclosed herein that confers resistance to peanut smut and methods of making the peanuts. In one embodiment, a peanut including the gene variant that confers resistance to peanut smut is provided. The gene variant includes the resistant allele identified in Table 1 above. The peanut may be made using traditional breeding techniques. That is, the peanuts of the present disclosure may be bred using traditional plant breeding methods known in the art. For example, traditional plant breeding methods include, but are not limited to, recurrent selection, mass selection, bulk selection, crossbreeding, back-crossing, pedigree breeding, and genetic marker-assisted selection.

In another embodiment, the peanuts of the present disclosure can be bred using transgenic breeding. In this embodiment, the peanut can be produced by introducing a transgene conferring peanut smut resistance into a peanut plant. A "transgene," as used herein, refers to any DNA sequence, whether from a different species or from the same species, which is introduced into the genome using transformation or various breeding methods. Introduction of the transgene into the peanut plant may be performed using any genetic engineering technique known in the art. Examples include, but are not limited to, expression vectors introduced into plant tissues using a direct gene transfer method, such as microprojectile-mediated delivery, DNA injection, electroporation, and the like. In other embodiments, expression vectors are introduced into plant tissues by using either microprojectile-mediated delivery with a biolistic device or by using *Agrobacterium*-mediated transformation.

Moreover, the present disclosure includes kits and reagents for detection, identification, and/or creation of peanut smut resistance in a line of peanuts. In one embodiment, the kit includes a sample collection apparatus, such as those devices used for collecting or preserving a biological sample. In some embodiments, the kit includes a means of detecting expression profiles of specific panels of genes. For example, the kit includes means for detecting the presence of a peanut-smut resistance gene, such as the gene variant described herein. The kit may also include one or more probes.

In some embodiments, the kit can include one or more reagents useful for detection of the level of a resistance gene variant in the biological sample. The one or more reagents can be immobilized to a solid support. Non-limiting examples of the composition of the solid support structure include plastic, cardboard, glass, plexiglass, tin, paper, or a combination thereof. The solid support can also include a dip stick, spoon, scoopula, filter paper or swab. In one embodiment, the kit can include a container that contains the one or more reagents.

The reagents can include a labeled compound or agent capable of detecting an expressed resistance gene variant (e.g., an scFv or monoclonal antibody) in a biological sample; means for determining the amount of gene expression in the sample; and means for comparing the amount of gene expression in the sample with a standard, such as a control sample or threshold. In one embodiment, the control sample is a cell from a plant known to be resistant to peanut smut infection. In another embodiment, the control sample can be a cell from a plant known to be susceptible to peanut smut infection. The compound or agent can be packaged in a suitable container.

The kit can further include instructions for using the kit to detect peanut smut resistance in a sample. The kit can include informational material for using the kit to assess and confirm peanut smut resistance. The informational material can be descriptive, instructional, marketing, or other material that relates to the methods described herein. The informational material of the kits is not limited in its form. In one embodiment, the informational material can include information about production of the components of the kit, such as molecular weight, concentration, date of expiration, batch, or production site information, and so forth. In one embodiment, the informational material relates to methods of using the components of the kit. The information can be provided in a variety of formats, include printed text, computer readable material, video recording, or audio recording, or information that provides a link or address to substantive material.

In some embodiments, the kit can also include one or more primers for amplifying at least one nucleic acid sequence within the gene sequence described herein. For example, the control samples can include nucleic acids that hybridize to the primers.

The kit can also include other ingredients, such as solvents or buffers, a stabilizer, or a preservative. Optionally, the kit can include therapeutic agents that can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Methods and Materials

To identify region(s) of the peanut genome responsible for smut resistance, two recombinant inbred line (RIL) peanut populations comprised of a peanut smut resistant strain and a peanut smut susceptible strain were bred. FIG. 2 is a graphical representation showing the method of breeding for the two RIL populations. The smut-susceptible parent labeled "Granoleico" was used as the validation population while the smut-susceptible parent labeled "10_2870" was used as the mapping population. The smut-resistant parent is labeled as "Ascasubi."

The two RIL populations and their parental lines were phenotyped for resistance to smut. The mapping population was phenotyped in 2020 and the validation population was phenotyped in 2021. The populations were planted in heavily infested soils in General Deheza, Cordoba, Argentina and grown under rainfed conditions. The populations were planted in an augmented grid design with three replications (single plants as experimental units). Pods were opened by hand and rated for disease incidence, which was determined by the presence of *T. frezzii sori* or spore masses on the kernels. The disease incidence (DI) was calculated as DI=infected pods/total pods.

The RIL individuals were then sequenced using iGenomX RipTide library preparation and Illumina NovaSeq sequencing to yield approximately one times genome coverage. Complete parental genomes were obtained using PacBio HIFI sequencing. Phenotypic and genotypic data were analyzed using Applicant's computational tool, Khufu.

Results

Analysis of the mapping population resulted in the identification of a QTL associated with smut resistance on chromosome 12. The QTL was verified by genotyping and phenotyping the validation population, as shown in FIG. 3. FIG. 3 shows the results of screening and sorting the population individuals for the contribution of smut-resistant variety haplotypes (Ascasubi) in the QTL region and the contribution of smut-susceptible elite variety haplotypes (Granoleico) in the rest of the genome.

Within the QTL, a region containing a "R" gene cluster was found in the smut-resistant parent, Ascasubi, but was missing in the smut-susceptible parents, 10_2870 and Granoleico. These results indicate the presence of a smut-resistant gene that can be used to develop smut resistant peanut varieties faster and more efficiently using molecular assisted breeding strategies.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. A method of identifying a recombinant inbred peanut line that is resistant to peanut smut, comprising:
   - obtaining a biological sample from at least one peanut in the recombinant inbred peanut line;
   - performing whole genome sequencing on at least a portion of the biological sample to generate at least one target sequence;
   - comparing the at least one target sequence to a peanut reference sequence, wherein the peanut reference sequence comprises SEQ ID NO. 4; and
   - identifying the recombinant inbred peanut line as being resistant to peanut smut if the at least one target sequence is identical to the peanut reference sequence.

2. The method of claim 1, wherein the peanut reference sequence comprises a single nucleotide polymorphism (SNP) at position 178 of SEQ ID NO. 4.

3. The method of claim 2, wherein the SNP comprises a substitution of an adenine for a guanine.

4. The method of claim 1, wherein the recombinant inbred peanut line is resistant to peanut smut caused by colonization of *Thecaphora frezzii.*

5. A method of producing a smut resistant peanut plant or a part thereof, comprising:
   - crossing a peanut plant having a resistance gene associated with smut resistance with itself or a second peanut plant, wherein the resistance gene comprises a sequence identical to SEQ ID NO: 4;
   - harvesting a resulting peanut seed; and
   - growing the peanut seed to produce the smut resistant peanut plant or part thereof.

6. The method of claim 5, wherein the peanut plant is obtained from a recombinant inbred line of peanuts.

7. The method of claim 5, wherein the smut resistant peanut plant is resistant to peanut smut caused by colonization of *Thecaphora frezzii.*

8. The method of claim 5, further comprising employing the smut resistant peanut plant as a source of breeding material.

9. A smut-resistant peanut plant or part thereof produced according to the method of claim 5.

10. A method of treating or preventing peanut smut infestation in a geographic region in need thereof, comprising:
    - producing a recombinant inbred line of smut resistant peanuts, wherein at least one peanut from the recombinant inbred line comprises a gene resistant to peanut smut and the gene resistant to peanut smut comprises a sequence having 100 percent identity to SEQ ID NO: 4; and
    - cultivating the recombinant inbred line of smut-resistant peanuts in the geographic region.

11. The method of claim 10, wherein the recombinant inbred line of smut-resistant peanuts is resistant to peanut smut caused by colonization of *Thecaphora frezzii.*

12. The method of claim 10, wherein the cultivating step further comprises growing the recombinant inbred line of smut-resistant peanuts under plant growth conditions.

* * * * *